(12) United States Patent
Androulakis et al.

(10) Patent No.: US 12,296,645 B2
(45) Date of Patent: May 13, 2025

(54) OCCUPANT CLOTHING PREDICTOR FOR THERMAL EFFECTOR CONTROL

(71) Applicant: Gentherm Incorporated, Novi, MI (US)

(72) Inventors: Ioannis Androulakis, Livonia, MI (US); Blake Thomas Martin, Troy, MI (US)

(73) Assignee: Gentherm Incorporated, Novi, MI (US)

( * ) Notice: Subject to any disclaimer, the term of this patent is extended or adjusted under 35 U.S.C. 154(b) by 303 days.

(21) Appl. No.: 17/800,659

(22) PCT Filed: Mar. 18, 2021

(86) PCT No.: PCT/US2021/022876
§ 371 (c)(1),
(2) Date: Aug. 18, 2022

(87) PCT Pub. No.: WO2021/206887
PCT Pub. Date: Oct. 14, 2021

(65) Prior Publication Data
US 2023/0079510 A1  Mar. 16, 2023

Related U.S. Application Data

(60) Provisional application No. 63/007,047, filed on Apr. 8, 2020.

(51) Int. Cl.
*B60H 1/00* (2006.01)
*A61B 5/107* (2006.01)
(Continued)

(52) U.S. Cl.
CPC ....... *B60H 1/00742* (2013.01); *A61B 5/1072* (2013.01); *B60N 2/0024* (2023.08);
(Continued)

(58) Field of Classification Search
CPC .............. B60H 1/00742; A61B 5/1072; A61B 2562/0247; B60N 2/0024; B60N 2/0025;
(Continued)

(56) References Cited

U.S. PATENT DOCUMENTS 5,877,677 A * 3/1999 Fleming ............. G01G 19/4142
340/436
6,345,839 B1 * 2/2002 Kuboki .................. B60N 2/002
73/862.632

(Continued)

OTHER PUBLICATIONS

International Search Report and Written Opinion for International Patent Application No. PCT/US2021/022876 completed on May 21, 2021.

(Continued)

*Primary Examiner* — Navid Z. Mehdizadeh
*Assistant Examiner* — Caitlin R McCleary
(74) *Attorney, Agent, or Firm* — Carlson, Gaskey & Olds, P.C.

(57) ABSTRACT

A microclimate control system for a seated occupant includes a seat having a cushion and a back respectively including a first array of pressure sensors and a second array of pressure sensors. The first array of pressure sensors provides a cushion occupant output. The second array of pressure sensors provides a back occupant output. The cushion and back occupant outputs correspond to load distributions from the seated occupant. At least one thermal effector is configured to provide thermal conditioning to the seated occupant. A controller is in communication with the first and second arrays of pressure sensors and with the at least one thermal effector. The controller includes an occupant personal parameters algorithm configured to extract occupant personal parameters based upon the cushion and back occupant outputs. The occupant personal parameters include at least two of an occupant weight, an occupant (Continued)

height, and an occupant gender. The occupant personal parameter algorithm estimates an occupant clothing insulation value from the occupant personal parameters. The controller is configured to regulate the at least one thermal effector based upon the occupant clothing insulation value.

17 Claims, 4 Drawing Sheets

(51) Int. Cl.
 *B60N 2/00* (2006.01)
 *B60N 2/56* (2006.01)
 *B62D 1/06* (2006.01)
(52) U.S. Cl.
 CPC ........... *B60N 2/0025* (2023.08); *B60N 2/003* (2023.08); *B60N 2/56* (2013.01); *A61B 2562/0247* (2013.01); *B60N 2210/40* (2023.08); *B62D 1/065* (2013.01)

(58) Field of Classification Search
 CPC ...... B60N 2/003; B60N 2/56; B60N 2210/40; B60N 2/0268; B62D 1/065
 See application file for complete search history.

(56) References Cited

U.S. PATENT DOCUMENTS

| | | | |
|---|---|---|---|
| 2011/0241860 A1 | 10/2011 | Andrews et al. | |
| 2015/0025738 A1* | 1/2015 | Tumas | B60H 1/00742 701/36 |
| 2017/0334263 A1* | 11/2017 | Schumacher | B60H 1/00292 |
| 2018/0325264 A1 | 11/2018 | Gallagher et al. | |
| 2019/0038147 A1 | 2/2019 | Perraut et al. | |
| 2022/0388370 A1* | 12/2022 | Pihlsgård | B60H 1/00742 |

OTHER PUBLICATIONS

International Preliminary Report on Patentability for International Patent Application No. PCT/US21/22876 issued on Oct. 6, 2022.

\* cited by examiner

OCCUPANT CLOTHING PREDICTOR FOR THERMAL EFFECTOR CONTROL

CROSS-REFERENCE TO RELATED APPLICATION

This application claims priority to U.S. Provisional Patent Application No. 63/007,047 which was filed on Apr. 8, 2020.

BACKGROUND

Vehicles commonly include heating, ventilation and air conditioning (HVAC) systems to thermally condition air within the vehicle's cabin. A typical modern vehicle also includes seats having thermal effectors that are controlled to achieve occupant thermal comfort. The thermal effectors may include heating and/or cooling elements that further heat or cool the occupant through the seat support surfaces.

Although many systems have been proposed, it has been difficult to achieve a commercial seating thermal control system that effectively and efficiently achieves occupant thermal comfort using the seat, particularly for the numerous variable conditions present in a vehicle cabin.

Vehicle microclimate control systems, which incorporate the seats, are used in vehicles to personalize the thermal comfort to an occupant. These systems can be relatively complex and are dependent upon the occupant's clothing when determining the amount of heating or cooling needed to achieve occupant personal comfort. Clothing acts as insulation, so unsurprisingly, the clothing worn by the occupant can greatly impact the heat transfer between the occupant and the surrounding microclimate thermal effectors, which reduces the effectiveness and personalization of the system if not properly accounted for.

SUMMARY OF THE INVENTION

In one exemplary embodiment a microclimate control system for a seated occupant includes a seat including a cushion and a back respectively including a first array of pressure sensors and a second array of pressure sensors, the first array of pressure sensors configured to provide a cushion occupant output, the second array of pressure sensors configured to provide a back occupant output, the cushion and back occupant outputs corresponding to load distributions from the seated occupant, at least one thermal effector configured to provide thermal conditioning to the seated occupant, a controller in communication with the first and second arrays of pressure sensors and with the at least one thermal effector, the controller including an occupant personal parameters algorithm configured to extract occupant personal parameters based upon the cushion and back occupant outputs, the occupant personal parameters including at least two of an occupant weight, an occupant height, and an occupant gender, wherein the occupant personal parameter algorithm estimates an occupant clothing insulation value from the occupant personal parameters, and wherein the controller is configured to regulate the at least one thermal effector based upon the occupant clothing insulation value.

In another example of the above described microclimate control system for a seated occupant at least one of the first and second arrays of pressure sensors is arranged in one of a T-shaped configuration, and a L-shaped configuration.

In another example of any of the above described microclimate control systems for a seated occupant the cushion occupant output corresponds to an occupant waist perimeter, and the occupant personal parameters algorithm determines an occupant fitness level from the waist perimeter.

In another example of any of the above described microclimate control systems for a seated occupant the cushion and back occupant outputs correspond to an occupant center of gravity, the occupant personal parameters algorithm inferring the occupant gender from the occupant center of gravity.

In another example of any of the above described microclimate control systems for a seated occupant the occupant personal parameters algorithm infers the occupant height from at least one of a pressure distribution on the cushion occupant output and a pressure distribution on the back occupant output.

Another example of any of the above described microclimate control systems for a seated occupant further includes an environmental sensor exposed to air outside of a vehicle, the environmental sensor is configured to provide environmental data based upon at least one of outside air temperature and outside humidity, the controller is in communication with the environmental sensor, and the occupant personal parameters algorithm is configured to estimate the occupant clothing insulation value based upon the environmental data.

In another example of any of the above described microclimate control systems for a seated occupant the thermal effectors are selected from the group comprising a climate controlled seat, a head rest/neck conditioner, a climate controlled headliner, a steering wheel, a heated gear shifter, a heater mat, and a mini-compressor system.

Another example of any of the above described microclimate control systems for a seated occupant further includes a navigation system configured to provide a vehicle location, the navigation system being in communication with the controller, the controller is configured to infer at least one of the occupant culture, the occupant region and/or the occupant habit from the vehicle location.

An exemplary method of controlling an occupant microclimate system, the method including the steps of measuring an occupant pressure distribution in a seat cushion and a seat back, extracting occupant personal parameters based upon the occupant pressure distribution, the occupant personal parameters including at least two of an occupant weight, an occupant height and/or an occupant gender, estimating an occupant clothing insulation value from the occupant personal parameters, and regulating at least one thermal effector based upon the occupant clothing insulation value.

In another example of the above described exemplary method of controlling an occupant microclimate system the extracting step includes a step of estimating an occupant waist perimeter and providing an occupant fitness level based on the estimated occupant waist perimeter.

In another example of any of the above described exemplary methods of controlling an occupant microclimate system the extracting step includes a step of estimating an occupant center of gravity and providing the occupant gender based at least in part on the occupant center of gravity.

In another example of any of the above described exemplary methods of controlling an occupant microclimate system the extracting step provides the occupant height from the occupant pressure distribution on at least one of the seat cushion and the seat back.

In another example of any of the above described exemplary methods of controlling an occupant microclimate system including a step of measuring air outside of a vehicle to provide environmental data based upon at least one of outside air temperature and outside humidity, and the estimating step includes estimating the occupant clothing insulation value based upon the environmental data.

In another example of any of the above described exemplary methods of controlling an occupant microclimate system the thermal effectors are selected from the group comprising a climate controlled seat, a head rest/neck conditioner, a climate controlled headliner, a steering wheel, a heated gear shifter, a heater mat, and a mini-compressor system.

In another example of any of the above described exemplary methods of controlling an occupant microclimate system including a step of determining a vehicle location, the extracting step providing at least one of the occupant culture, the occupant region and/or the occupant habit from the vehicle location.

BRIEF DESCRIPTION OF THE DRAWINGS

The disclosure can be further understood by reference to the following detailed description when considered in connection with the accompanying drawings wherein.

The embodiments, examples and alternatives of the preceding paragraphs, the claims, or the following description, drawings, and slides, including any of their various aspects or respective individual features, may be taken independently or in any combination. Features described in connection with one embodiment are applicable to all embodiments, unless such features are incompatible.

DETAILED DESCRIPTION

Clothing insulation is to a large extent an unused parameter in thermal comfort systems, although it is a very significant one. Generally, thermal comfort related testing in the automotive sector over-regulates based upon clothing. Furthermore, existing computer simulated models of thermal comfort are evaluated at a specific value of clothing insulation, providing a "one size fits all" approach. The disclosed invention offers a method of predicting a clothing level of the occupant and customize the activation and control strategy of components providing thermal comfort (i.e., thermal effectors including seat heaters, neck warmer, etc).

The control strategy disclosed herein is based upon the assumption that humans are expected to add or remove clothing insulation to their bodies according to environmental and personal physiological parameters. According to the Harris-Benedict principle, such personal physiological parameters include weight, height, gender, age, and fitness level. Several such parameters can be directly measured or evaluated, but the cost of direct measurement is prohibitive in a typical vehicle application. In order to make the determination of clothing more cost-effective, the control strategy relies upon simple, inexpensive pressure sensors on or near the surface of the seat. The pressure sensors are used to generate information on weight, height, gender, etc. based upon the pressure distribution on the seat surface. Furthermore, a reading of the environmental temperature is used, and other available information may also be referenced. The data is then fed into an algorithm (estimator 50 in FIG. 2) that estimates an occupant clothing insulation value 52 for a seated occupant. This clothing insulation value is then be used for the thermal comfort models used to control the thermal effectors, which provide a more accurate personal occupant comfort. In some examples, the estimator 50 can be local to a vehicle ECU. In other examples, the estimator 50 can be remote from the vehicle and some or all of the calculations are performed via a distributed computing service, cloud computing, and/or a remote processor.

Figure 1:
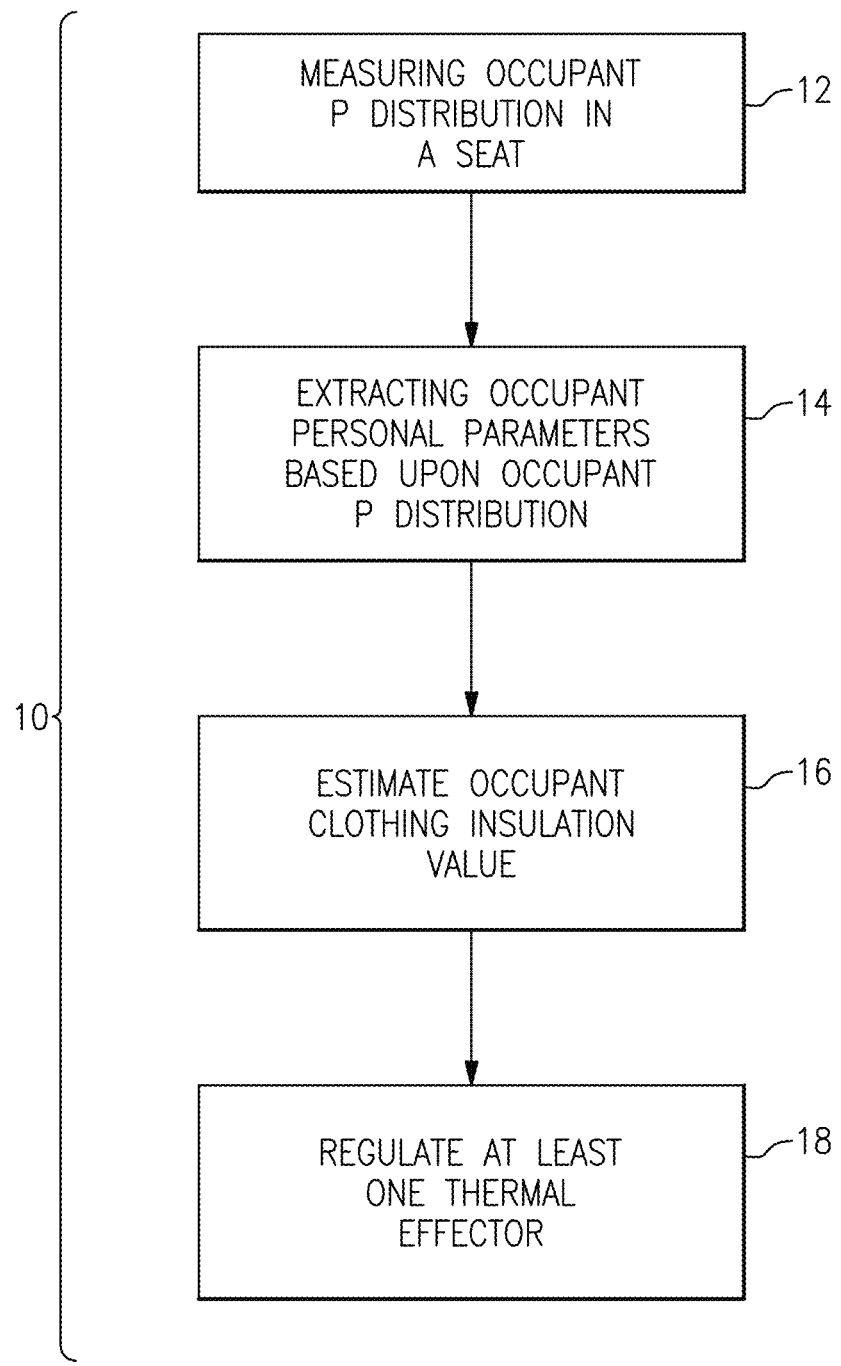
FIG. 1 is a flow chart depicting an example method of controlling an occupant microclimate system.
Figure 2A:
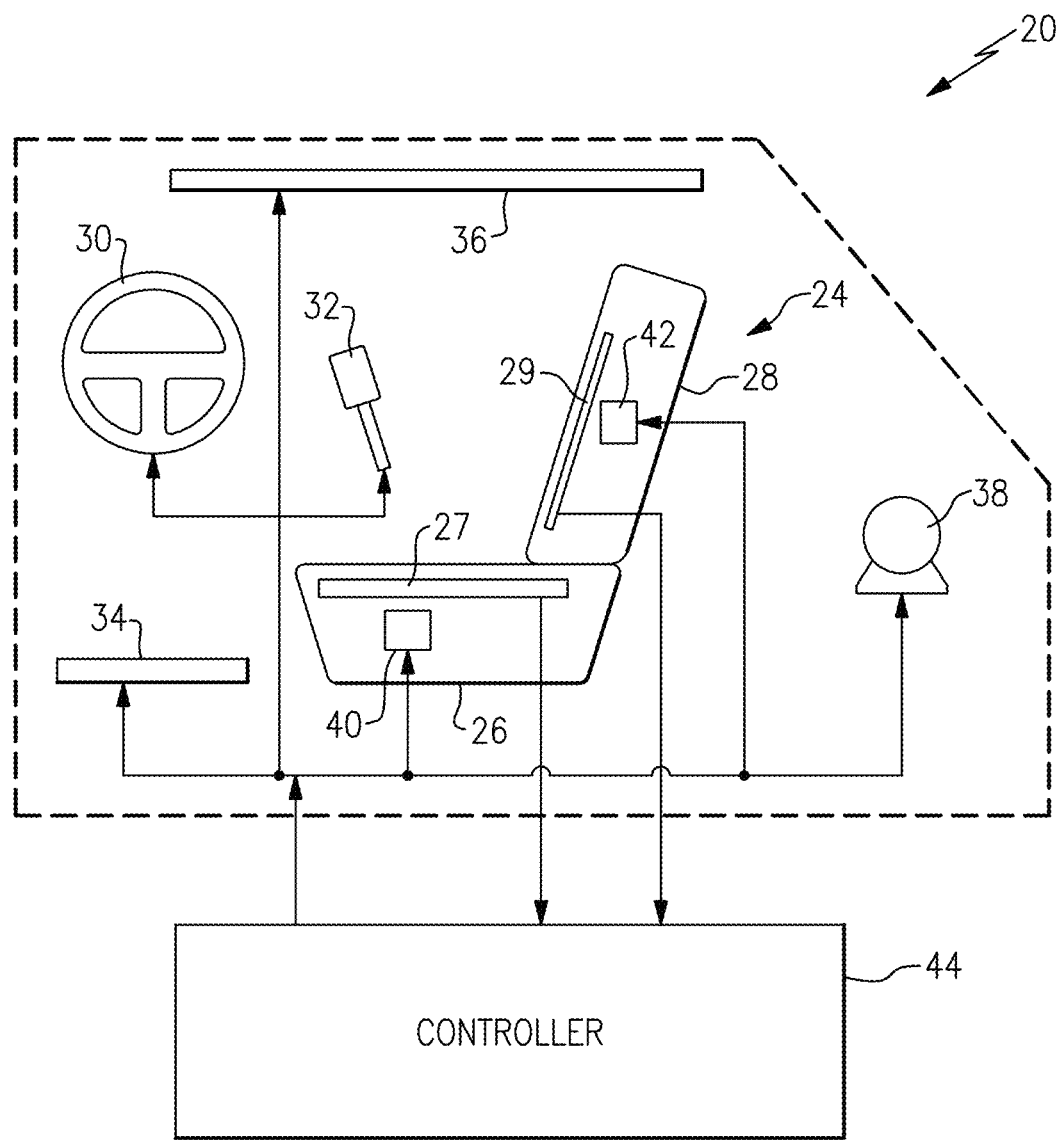
FIG. 2A is a schematic depicting a vehicle microclimate control system for a seated occupant.
Figure 2B:
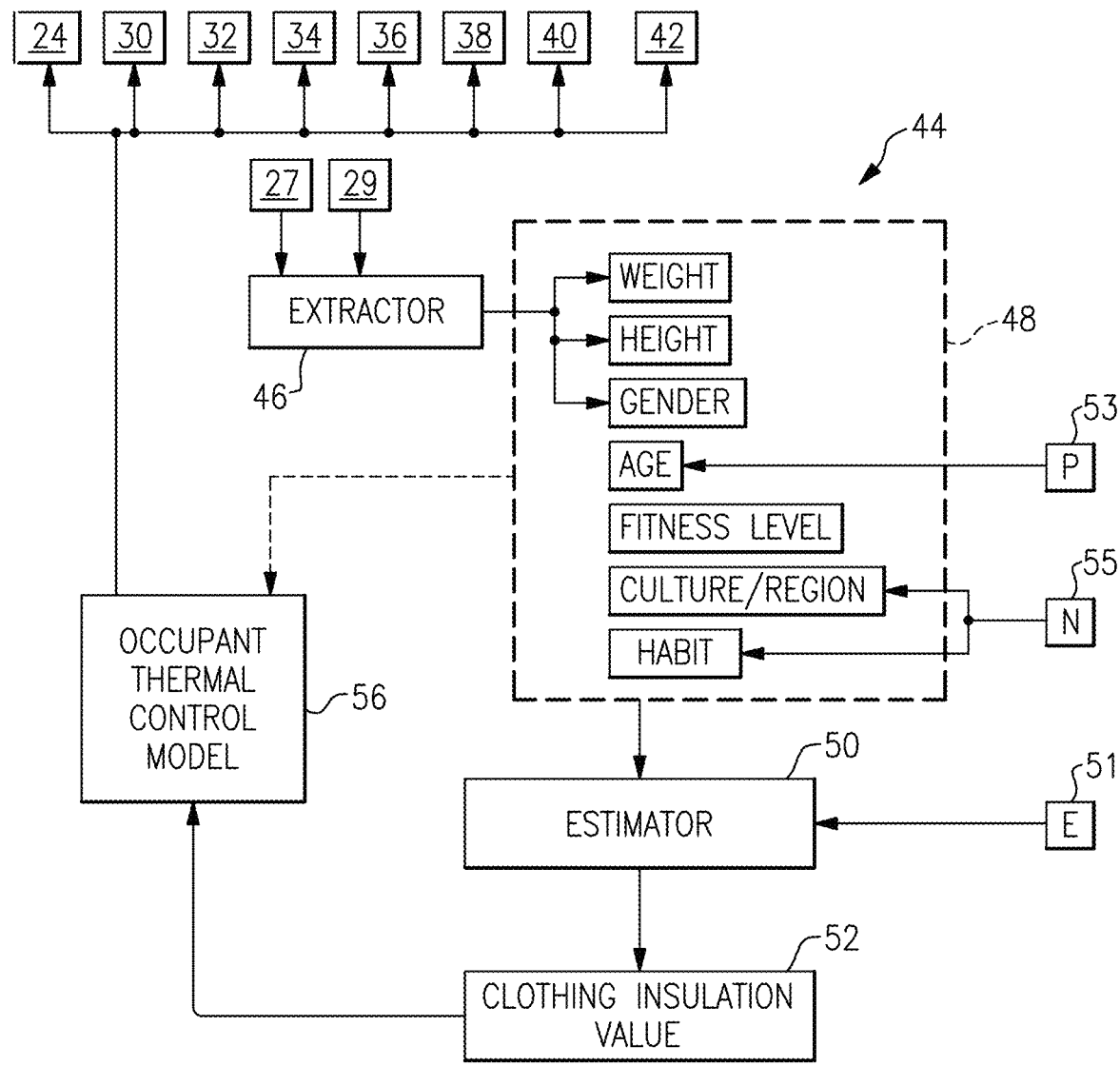
FIG. 2B schematically illustrates the controller used for the vehicle microclimate control system.

FIG. 1 illustrates a method 10 of controlling an occupant microclimate system 20 for a vehicle, shown in FIGS. 2A and 2B. With continuing reference to FIG. 1, an occupant pressure distribution on a seat is measured, as indicated at block 12. Occupant personal parameters are extracted from the measurement based upon the occupant pressure distribution on the seat, as indicated at block 14. The occupant personal parameters include, for example, an occupant weight, an occupant height, and an occupant gender. These occupant personal parameters (48 in FIG. 2B) are used (along with occupant age, an occupant culture, occupant region, and/or an occupant habit derived from other inputs) to estimate an occupant clothing insulation value, as indicated at block 16. The occupant clothing insulation value effects the ability of the vehicle microclimate control system 20 to accurately control the various thermal effectors within the system. One or more of the thermal effectors are regulated based upon the occupant clothing insulation value, as indicated at block 18.

An example portion of a vehicle microclimate control system 20 is shown in more detail in FIG. 2A. A seat 24 includes a cushion 26 and a back 28 that supports an occupant. The cushion 26 includes a first array of pressure sensors 27, and the back 28 includes a second array of pressure sensors 29. The first and second arrays of pressure sensors 27, 29 measure an occupant pressure distribution from which the occupant personal parameters can be extracted. Cushion and back occupant outputs are provided by the first and second arrays of pressure sensors 27, 29 to provide a load distribution. It should be understood that either load or pressure may be provided by the sensors, and these terms may be used interchangeably in this disclosure. The system 20 includes a controller 44 that may comprise one or more processors and hardware and/or software. In some examples, the controller 44 includes communication hardware for communicating data with a remote processing system. The controller 44, shown in more detail in FIG. 2B, includes an extractor 46 that is in communication with the first and second arrays of pressure sensors 27, 29. The extractor 46 receives the pressure signals from the arrays and compares the cushion and back occupant outputs to one or more models to extract the occupant personal parameters 48. These models may be determined empirically by performing a linear regression on a training data set for each of the occupant personal parameters. An example regularized linear regression over activated k sensors is as follows: $y = a + \theta_1 x_1 + \theta_2 x_2 + \ldots + \theta_k x_k$ With the constriction to minimize the cost function, $$J(\theta) = MSE(\theta) + \frac{\lambda}{2} \sum_{i=1}^{k} \theta_i^2,$$

where MSE is the mean squared error which is a function of the set of coefficients $\theta=\{\theta_1, \theta_2, \ldots \theta_k\}$ of the input vector x with k components, and $\lambda$ is a regularization constant.

The accuracy of the training set is then evaluated during development of the models based upon a test set to corroborate the model.

In one example, data from the cushion and back occupant outputs correspond to occupant anthropometric characteristics which may then be used to infer at least one of occupant weight, occupant height and occupant gender. Inputs from pressure sensors at particular locations may be given greater weight in the analysis.

Occupant weight is inferred from the summation of the magnitude of the pressure sensed by the back and cushion pressure sensors. Fewer sensors sensing a lower pressure would be indicative of a lighter occupant, whereas more sensors sensing a comparatively higher pressure would be indicative of a heavier occupant.

Data from the cushion and back occupant outputs is also used in some examples to determine occupant center of gravity from which the gender may be inferred. Studies indicate that the center of gravity for a female is approximately one inch lower than that of the male. This difference in center of gravity is sensed by the pressure distributions on the cushion 26 and the back 28.

The occupant height is inferred from the pressure distribution on the cushion. Typically, a taller person will have a more concentrated pressure distribution at the rear of the seat where the cushion meets the back. Additionally, the occupant height may also be inferred from the pressure distribution on the back which manifests itself in pressure being sensed at a location farther from the cushion which is indicative of a taller occupant. Of course, the amount of clothing an occupant may wear is typically affected by environmental conditions. More clothing is generally worn in colder temperatures, and less clothing is generally worn in warmer temperatures. To this end, an environmental sensor 51 is exposed to air outside of the vehicle. The environmental sensor provides environmental data, which may be provided over a CAN or LIN bus, based upon at least one of outside air temperature and outside humidity. It should be understood that the environmental data may instead be provided by a transfer function based upon other inputs indicative of outside air in some examples. This environmental data is used to infer the effects of clothing selection by the occupant which may be used to adjust the occupant clothing insulation value beyond the value estimated from the pressure distribution on the seat.

The occupant personal parameters that the extractor is able to determine from the seat are limited (e.g., weight, height and gender). The limitation affects the accuracy of the clothing insulation value estimate. This estimate can be made more accurate by providing additional occupant personal parameters, such as occupant age, occupant culture/region and/or occupant habit, to the estimator 50.

Personalized devices 53, such as cell phones and watches, are also able to communicate with the controller 44 to provide relevant data to the estimator 50. Such data may include occupant age or location data from navigational tools 55, which can be used to determine occupant culture/region and/or occupant habits. Occupant fitness may be provided as an additional occupant personal parameter, for example, using heart rate variability (HRV) indices. The assessment cannot be done in a one-off fashion; an occupant is tracked over a period of time and then compared against a database/known data. Personal devices like watches or fitness trackers are suitable for this purpose. The comparison can be local to the vehicle or remote via a distributed computing system. The fitness level aspect of the estimator algorithm can be used when the statistical confidence becomes significant.

The amount of clothing worn by the occupant may also be affected by cultural preferences and regional considerations. That is, some cultural/regional preferences may indicate less or more clothing is worn by the occupant. To this end, the navigation tools 55 is used in some examples to provide the occupant and/or vehicle location, which can be used to infer the climate, region, culture and/or environmental data.

The vehicle location can be used to infer occupant habits, such as the occupant habitually visiting a fitness center, which can affect the occupant's clothing choices. For example, the occupant may be hot and sweaty when leaving a fitness center such that less clothing is worn by the occupant than would otherwise be predicted from the environmental data and/or the estimated occupant clothing insulation value.

The clothing insulation value 52 may be provided to the thermal control model as a class or category. One example classification is provided in the Table below, which is a byproduct of performing a nonlinear regression analysis on data including environmental temperature, weight, height and gender.

| CLASS | CLOTHING VALUE | CLOTHING CONDITION |
|-------|----------------|---------------------|
| 0 | <0.6 | Little clothing |
| 1 | 0.6-0.8 | |
| 2 | 0.8-1.0 | Moderate clothing |
| 3 | 1.0-1.2 | |
| 4 | >1.2 | Heavily clothed |

The disclosed method and system is able to estimate the clothing insulation value due to the strong correlation captured by the combined effect of environmental temperature, occupant height, occupant weight, occupant gender. This correlation may be further strengthened by also providing age and other occupant personal parameters as inputs into the estimator 50, although these additional occupant personal parameters generally have only a slight effect on the estimated clothing insulation value compared to the combined effect of environmental temperature, occupant height, occupant weight, and occupant gender.

Ultimately, the clothing insulation value 52 is fed into an occupant thermal control module 56 that is used to regulate the various thermal effectors. One or more individual occupant personal parameters 48 may be fed into the thermal control module 56 for use. The thermal effectors include, for example, the seat 24, a steering wheel 30, a shifter 32, a mat 34 (such as a floor mat, a door panel, and/or a dash panel), a headliner 36, a microcompressor system 38, a cushion thermal conditioner 40, and/or a back/neck/head thermal conditioner 42. The occupant thermal control model 56 may be based upon equivalent homogeneous temperature (EHT), which uses the clothing insulation value 52 in its modeling of the heat transfer between the occupant and the occupant's environment. Of course, approaches other than those based upon EHT may be used to achieve occupant thermal comfort.

Particular areas of occupant contact with the seat are more useful than others for discerning occupant personal parameters. For example, pressure sensors placed vertically higher in the seat back are suitable for capturing height variations, whereas other pressure sensors in the back may assist in regressing weight distribution. Example pressure sensor distribution arrangements are illustrated for the seats 24, 124 respectively shown in FIGS. 3A and 3B. A first group of sensors is arranged fore/front-aft/rear, and a second group of sensors is arranged laterally or side-to-side. The laterally arranged sensors may be useful in determining waist perimeter, which can be an indicator of body fat/muscle content. By using strategically arranged groups of sensors, a more inexpensive pressure sensing scheme may be provided rather than using a large mat of sensors.

Figure 3A:
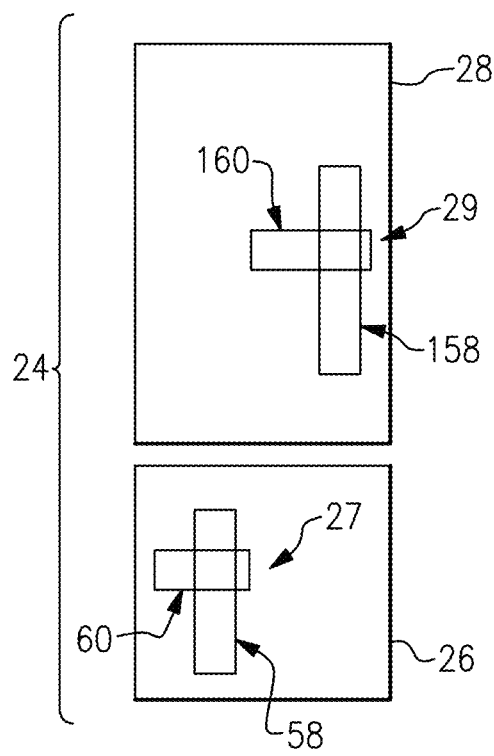
FIG. 3A is a schematic of a seat illustrating a first arrangement of first and second arrays of pressure sensors on a seat.
Figure 3B:
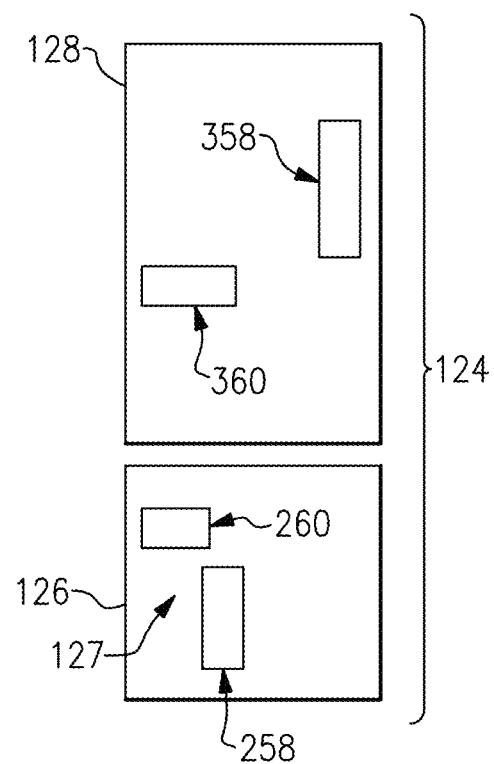
FIG. 3B is a schematic of a seat illustrating a second arrangement of first and second arrays of pressure sensors on another seat.

Referring to the seat 24 in FIG. 3A, the first array of pressure sensors 27 includes first and second groups 58, 60 of pressure sensors arranged in a T-shaped configuration. Similarly, the back 28 may have its second array of pressure sensors 29 arranged in a T-shaped configuration provided by first and second groups of sensors 158, 160. Another example is illustrated in FIG. 3B. The first array of pressure sensors 127 is provided by an L-shaped configuration of a first and second group of sensors 258, 260. The discrete first and second group 258, 260 are spaced apart and separated from one another, rather than the overlapping arrangement of groups of sensors shown in FIG. 3A. Similarly, the back 128 includes a second array of sensors 128 comprised of first and second groups of sensors 358, 360 arranged in an L-shaped configuration. It should also be understood that the arrangement of sensors illustrated in the backs and cushions of FIGS. 3A and 3B may be interchanged, e.g., the cushion 26 with the back 128, and the cushion 126 with the back 28.

Capturing thermo-physiological thermal comfort differences based on weight, height, gender, clothing, and body structure allows climate system designers to fine-tune hardware. For example, an occupant having a heavily clothed upper body may not require the same heating power at the back heater mat, creating an opportunity to decrease power consumption. So, with the body structure identified, as an example, a smaller area of the heat mat can be activated for a tall skinny person, as opposed to an individual with a wide torso and narrow pelvis or combinations of the aforementioned.

It should also be understood that, although a particular component arrangement is disclosed in the illustrated embodiment, other arrangements will benefit herefrom. Although particular step sequences are shown, described, and claimed, it should be understood that steps may be performed in any order, separated or combined unless otherwise indicated and will still benefit from the present invention.

Although the different examples have specific components shown in the illustrations, embodiments of this invention are not limited to those particular combinations. It is possible to use some of the components or features from one of the examples in combination with features or components from another one of the examples.

Although an example embodiment has been disclosed, a worker of ordinary skill in this art would recognize that certain modifications would come within the scope of the claims. For that reason, the following claims should be studied to determine their true scope and content.

What is claimed is:

1. A microclimate control system for a seated occupant, comprising:
    a seat including a cushion and a back respectively including a first array of pressure sensors and a second array of pressure sensors, the first array of pressure sensors configured to provide a cushion occupant output, the second array of pressure sensors configured to provide a back occupant output, the cushion and back occupant outputs corresponding to load distributions from the seated occupant;
    at least one thermal effector configured to provide thermal conditioning to the seated occupant;
    computing hardware in communication with the first and second arrays of pressure sensors and with the at least one thermal effector, the computing hardware configured to utilize an occupant personal parameters algorithm to extract occupant personal parameters based upon the cushion and back occupant outputs, the occupant personal parameters including at least two of an occupant weight, an occupant height, and an occupant gender;
    wherein the computing hardware is configured to utilize the occupant personal parameter algorithm to estimate an occupant clothing insulation value from the occupant personal parameters; and
    wherein the computing hardware is configured to regulate the at least one thermal effector based upon the occupant clothing insulation value.

2. The system of claim 1, wherein at least one of the first and second arrays of pressure sensors is arranged in one of a T-shaped configuration, and a L-shaped configuration.

3. The system of claim 1, wherein the cushion occupant output corresponds to an occupant waist perimeter, and the computing hardware is configured to utilize the occupant personal parameters algorithm to determine an occupant fitness level from the waist perimeter.

4. The system of claim 1, wherein the cushion and back occupant outputs correspond to an occupant center of gravity, the computing hardware is configured to utilize the occupant personal parameters algorithm to infer the occupant gender from the occupant center of gravity.

5. The system of claim 1, wherein the computing hardware is configured to utilize the occupant personal parameters algorithm to infer the occupant height from at least one of a cushion pressure distribution on the cushion occupant output and a back pressure distribution on the back occupant output.

6. The system of claim 1, further comprising an environmental sensor exposed to air outside of a vehicle, the environmental sensor is configured to provide environmental data based upon at least one of outside air temperature and outside humidity, the computing hardware is in communication with the environmental sensor, and the computing hardware is configured to utilize the occupant personal parameters algorithm to estimate the occupant clothing insulation value based upon the environmental data.

7. The system of claim 1, wherein the at least one thermal effector is selected from the group comprising a climate controlled seat, a head rest/neck conditioner, a climate controlled headliner, a steering wheel, a heated gear shifter, a heater mat, and a mini-compressor system.

8. The system of claim 1, further comprising a navigation system configured to provide a vehicle location, the navigation system being in communication with the computing hardware, the computing hardware is configured to infer at least one of an occupant culture and/or an occupant habit from the vehicle location.

9. The system of claim 6, wherein the computing hardware is configured to: infer, based on the vehicle location being a fitness center and the occupant departing from a fitness center, that the occupant will have an increased body temperature and less clothing than would otherwise be predicted from the environmental data and/or the estimated occupant clothing insulation value.

10. A method of controlling an occupant microclimate system, the method comprising the steps of:
- measuring an occupant pressure distribution in a seat cushion and a seat back;
- extracting occupant personal parameters based upon the occupant pressure distribution, the occupant personal parameters including at least two of an occupant weight, an occupant height and/or an occupant gender;
- estimating an occupant clothing insulation value from the occupant personal parameters; and
- regulating at least one thermal effector based upon the occupant clothing insulation value.

11. The method of claim 10, wherein the extracting step includes a step of estimating an occupant waist perimeter and providing an occupant fitness level based on the estimated occupant waist perimeter.

12. The method of claim 10, wherein the extracting step includes a step of estimating an occupant center of gravity and providing the occupant gender based at least in part on the occupant center of gravity.

13. The method of claim 10, wherein the extracting step provides the occupant height from the occupant pressure distribution on at least one of the seat cushion and the seat back.

14. The method of claim 10, comprising a step of measuring air outside of a vehicle to provide environmental data based upon at least one of outside air temperature and outside humidity, and the estimating step includes estimating the occupant clothing insulation value based upon the environmental data.

15. The method of claim 10, wherein the at least one thermal effector is selected from the group comprising a climate controlled seat, a head rest/neck conditioner, a climate controlled headliner, a steering wheel, a heated gear shifter, a heater mat, and a mini-compressor system.

16. The method of claim 10, comprising a step of determining a vehicle location, the extracting step providing at least one of an occupant culture and/or an occupant habit from the vehicle location.

17. The method of claim 14, comprising: inferring, based on the vehicle location being a fitness center and the occupant departing from a fitness center, that the occupant will have an increased body temperature and less clothing than would otherwise be predicted from the environmental data and/or the estimated occupant clothing insulation value.

* * * * *